United States Patent [19]

Potts et al.

[11] Patent Number: 4,888,168

[45] Date of Patent: Dec. 19, 1989

[54] STABLE OPHTHALMIC PREPARATIONS CONTAINING ACETAZOLAMIDE

[75] Inventors: Angela C. Potts; Mark Gibson, both of Hampshire, England

[73] Assignee: American Cyanamid Company, Wayne, N.J.

[21] Appl. No.: 127,847

[22] Filed: Dec. 2, 1987

[30] Foreign Application Priority Data

Mar. 2, 1987 [GB] United Kingdom ............... 8704810

[51] Int. Cl.⁴ ............... A61K 31/74; A61K 31/745; A01N 43/82
[52] U.S. Cl. ............... 424/78; 424/83; 514/363; 514/912; 514/913; 514/914; 514/915
[58] Field of Search ............... 424/78, 83; 514/363, 514/912, 913, 914, 915

[56] References Cited

U.S. PATENT DOCUMENTS

| | | | |
|---|---|---|---|
| 4,271,143 | 6/1981 | Schoenwald | 424/78 |
| 4,474,751 | 10/1984 | Haslam | 424/78 |

FOREIGN PATENT DOCUMENTS

0033042  8/1981  European Pat. Off. ............... 424/78

*Primary Examiner*—Joseph L. Schofer
*Assistant Examiner*—Carmen Pili-Curtis
*Attorney, Agent, or Firm*—Kenneth J. Dow; Edward A. Conroy, Jr.

[57] ABSTRACT

There is provided a stable, ophthalmic aqueous composition for topical administration, comprising (a) acetazolamide and either (b) a pre-formed, pharmaceutically acceptable, aqueous gel or (c) an aqueous gel-forming liquid capable of forming a pharmaceutically acceptable gel in situ when applied topically to a patient; said composition having a pH of less than 5.0.

12 Claims, No Drawings

STABLE OPHTHALMIC PREPARATIONS CONTAINING ACETAZOLAMIDE

This invention relates to pharmaceutical preparations for topical application in the treatment of eye conditions and which are either pre-formed gels or liquids which gel in situ when applied to the patient. More particularly, the invention is concerned to provide such preparations which contain a dosage of acetazolamide suitable for the treatment of glaucoma.

Acetazolamide, or N-(5-sulphamoyl-1,3,4-thiadiazol-2-yl)acetamide to give it its full name, is an effective ocular hypotensive agent when it is administered systemically, and it is widely used for the treatment of glaucoma. However, the use of acetazolamide is commonly associated with undesirable side effects, including metabolic acidosis, lethargy, anorexia, paresthesias, nephrolithiasis and impotence.

In view of the undesirable side effects on patients which can be produced when acetazolamide is administered systemically, it has become recognized that there could be advantages in administering this drug topically.

Attempts have been made, therefore, to formulate acetazolamide as an aqueous solution which can be administered through an eye dropper. However these topically applied aqueous solutions of acetazolamide have been found to be ineffective in lowering intraocular pressure. It is difficult to achieve therapeutic levels of acetazolamide when it is applied in the form of eye drops, because acetazolamide is only slowly absorbed across the cornea of the eye, with the result that insufficient amounts of the drug may be taken up by the patient in the relatively short time that the drops containing the active ingredient remain in contact with the cornea.

An ophthalmic gel offers the possibility of improving the contact time between the cornea and the acetazolamide to ensure a sufficient dosage of the drug, and in a recently published paper reporting on a study to assess whether topical acetazolamide and methazolamide could be delivered by contact lenses, Friedman and his co-workers speculate on whether acetazolamide would be effective topically applied as a gel formation (Arch. Ophthalmol., 103 963–966, July 1985). Techniques for formulating gels for delivering ophthalmically active drugs topically are known in the art, see for example GB-A-No. 2013084 disclosing aqueous pre-formed pharmaceutical gels for application to the conjunctival sac of the eye, and GB-A-No. 1571832 and EP-A-No. 0126684 disclosing drug delivery systems in the form of liquids which gel in situ when warmed by the body of the patient and useful in the treatment of a variety of ocular conditions.

However, we have found that when an aqueous solution of acetazolamide is formulated into an aqueous gel at a pH in the range of 8.2–8.5, corresponding to the pH of the ophthalmic preparations used in the Friedman et al study, using gel-forming techniques known in the art, the resulting gels are insufficiently stable to be useful. Thus, in one accelerated storage experiment we determined, by HLPC, that the anticipated storage shelf-life (defined as the time for the potency of the acetazolamide to drop to 90% of its claimed potency) of an aqueous gel containing 1% by weight of the acetazolamide (pH=8.2-8.5) can be expected to be of the order only of 22 days at room temperature (23° C.). In a similar experiment, a gel containing 3.5% of the active ingredient (ph=8.9—a higher pH was needed in this experiment to solubilize the higher concentration of acetazolamide) was determined to have an anticipated storage shelf-life at 23° C. only of 7 days. Such degrees of instability are quite unacceptable.

Furthermore, we have found that reducing the pH of the gel, even down to pH 5.5, resulting in at least a substantial proportion of the acetazolamide being in the less preferred insoluble, free-acid form, does not result in any useful increase in stability. For example, based on an accelerated stability study at pH 5.5, the estimated useful shelf-life of the gel at 23° C. is about 13 weeks.

Despite these discouraging results, and despite the fact that it has hitherto been considered desirable to formulate at a relatively high pH in order to keep acetazolamide fully in solution, we have continued our investigations. Quite unexpectedly we have found that there is a dramatic and unpredicatable increase in the stability of aqueous gels containing acetazolamide at pH values below 5. Thus, based on solution studies, the predicated useful shelf-life at 25° C. of aqueous gels is still inadequate, whereas this has risen to over two years when the pH is dropped to 4.5, a satisfactory storage stability which is maintained, or even slightly improved, as the pH is dropped still further. At these relatively low pH values, the acetazolamide is only partly in solution.

Thus, the present invention broadly provides a stable ophthalmic aqueous composition for topical administration, comprising (a) acetazolamide and either (b) a pre-formed, pharmaceutically acceptable, aqueous gel or (c) an aqueous gel-forming liquid capable of forming a pharmaceutically acceptable gel in situ when applied topically to a patient; said composition having a pH of less than 5.0.

The preferred embodiment of the invention is a pre-formed gel. A number of high molecular weight gel-forming organic polymers are known to be suitable for the preparation of pre-formedppharmaceutical gels. We prefer to use high molecular weight carboxy vinyl polymers (MW above 1,000,000) such as those sold by B. F. Goodrich Company under the trade mark "Carbopol", and more especially Carbopol 934P of a molecular weight of about 3,000,000 and Carbopol 940 of a molecular weight of about 4,000,000. However, other gel-forming polymers can be used in this invention for the preparation of pre-formed gels, for example ethylene - maleic anhydride polymers and cellulose ethers such as hydroxypropylmethyl cellulose. As is well known, aqueous solutions of these acidic types of high molecular weight polymers form hydrogels when the pH of the solution is raised.

In accordance with this invention, the pH is to be adjusted to a level to cause the aqueous polymer solution to gel but is to be kept below pH 5 in order to secure a useful shelf-life. As mentioned above, we have found that maximum stability is achieved when the pH is maintained at pH 4.5 or below. However, since a pH of lower than pH 4 can damage eye tissue and provoke excessive lacrimation, we therefore prefer that the pH of the gel should lie in the range pH 4.0–4.5, and more preferable be about pH 4.3–4.5.

Alternatively, the compositions of the present invention can be formulated as aqueous liquids which are capable of forming a pharmaceutically acceptable gel in situ when applied topically to a patient. Preferably, in accordance with this aspect of the invention, there are used so-called "thermal gels", which are aqueous compositions which are liquids at room temperature but which are converted into gels in situ when warmed by the patient's body following topical application. Known aqueous thermal gel systems usually comprise polymers which have sol-gel transition temperatures typically in the range of 25°–40° C. Such systems using polymers known as "Pluronic" or "Tetronic" polymers have been described in the prior art. (see, for example, U.S. Pat. No. 4,188,373, UK-A-No. 1571832 and EP-A-No. 0126684). Such thermal gel systems are useful in the present invention, provided of course that the thermally gellable polymer chosen is one which is unaffected as to useful gelling properties at the low pH (below 5) which is used herein.

At pH values below 5, as used herein, the acetazolamide is only partially in solution, with the remainder forming a suspension in the pre-formed gel or in the thermosetting gel system. It is therefore important that the dispersed particles of the acetazolamide should be sufficiently small to minimize the risk of causing irritation to the eye of the patient. We have found that micronized acetazolamide with a particle size no greater than 20 microns, and preferably no greater than about 10 microns, should desirable be used.

It is preferred to incorporate an anti-microbial agent in the ophthalmic preparation of the invention to prevent microbial or fungal growth arising from contamination during use. A preferred antimicrobial agent is Chlorbutol B.P. (1,1,1-trichloro-2-methyl-2-propanol hemihydrate), although other antimicrobial agents which do not affect the stability of the composition, and which are compatible with the intended therapeutic use, can also be used.

Other conventional additives, such as ophthalmically acceptable surfactants, e.g. Polysorbate 80, and preservative enhancers, eg EDTA or its salts, can be included if desired.

The relative concentrations of the components of the present compositions are not especially critical. Typically, the acetazolamide will be incorporated in an amount of from 1 to 10% by weight, and preferably about 3.5%, same basis, in order to provide a useful unit dosage for the treatment of glaucoma. In the case of the preferred pre-formed gels, the concentration of the selected gel-forming polymer will be determined by the viscosity which it is desired that the gel should possess for easy application coupled with sufficient retention time in the patient. Suitably, the yield value of the gel, as determined by a Ferranti-Shirley viscometer at 25° C., ranges from 700 to 7000 dynes/cm$^2$. With Carbopol 934P, such yield values are obtained using concentrations of sterilized gel-forming polymer of about 0.5% to 5.0% by weight, the currently preferred concentration of this polymer being approximately 2.5% by weight. When a thermal gel vehicle is employed, it is preferred that the gel-forming polymer should be present in sufficient concentration to rapidly form a fairly righid gel upon topical application of the liquid composition to the patient. If the gelling time is too slow, then there is a risk of an unacceptable loss of acetazolamide from the treatment site.

If present, it is preferred that the antimicrobial agent should range from 0.12 to 0.70% by weight. We have found that about 0.5% by weight of Chlorbutol BP is satisfactory.

It is normally required that the ophthalmic preparation of the present invention should be presented in a sterile form. In order to achieve a sterile preformed gel, we prefer to pre-sterilize the individual ingredients and prepare the gel under aseptic conditions. We have found that post-sterilization of pre-formed gels by such conventional sterilization techniques as autoclaving and $\gamma$-irradiation are unsatisfactory since irreversible breakdown of the gel structure can occur.

A preferred technique for manufacturing a pre-formed ophthalmic gel of the invention is as follows:

Carbopl 934P is sterilized after hydration in a portion of the total water. Chlorbutol BP is dissolved in the remaining water and added to the Carbopol after sterilization by sterile filtration. Sterile micronised acetazolamide powder (particle size of 10 microns or less) is then thoroughly dispersed in the Carbopol. The gel is thickened to is final viscosity by slowly stirring in the sterile solution of sodium hydroxide, to give a final pH of 4.3 to 4.5. The gel can then be filled into suitable containers for administration, for example sterilized epoxy resin-lined aluminum ophthalmic tubes with latex seals. All of these manufacturing steps are conducted under strictly aseptic conditions in order to ensure a sterile final product.

Ophthalmic preparations in accordance with the preferred embodiments of this invention are effective in the treatment by topical application of glaucoma. Typically, the preparation is administered into the interior cul de sac of the eye, which in the case of pre-formed gels can easily be accomplished by distending the lower lid from the eye and applying a short ribbon of gel within the sac from a dispensing tube and then releasing the lid. The gellable liquid compositions of this invention can be supplied in bottles, or other suitable containers, and applied at the time of use by means of a conventional eye dropper.

The invention is illustrated by the Examples which follow:

EXAMPLE 1

The following gel was prepared under strictly aseptic conditions:

|  | % w/w |
| --- | --- |
| acetazolamide micronised (sterile) | 3.50 |
| chlorbutol B.P. | 0.50 |
| Carbopol 934P | 2.50 |
| NaOH (4% w/v solution) | 6.21 |
| water | 87.29 |

Sterile micronised acetazolamide powder, having an average particle size of 5 microns, with no particles in excess of 10 microns, was dispersed in a sterile unneutralized Carbopol in water containing chlorbutol in solution. As sterile 4% w/v sodium hydroxide solution was then added with constant mixing to a final pH of 4.3–4.5. The resultant gel has a yield value of 4100–4200 dynes/cm$^2$ by the Ferranti-Shirley viscometer at 25 deg.

The gel was filled into epoxy resin-lined aluminum ophthalmic tubes and stored at temperatures of 23° C., 37° C., 42° C. and 56° C., respectively. After two months storage there was no loss from initial acetazolamide potency, as determined by HPLC, at any of these storage temperatures.

EXAMPLE 2

The following gel was prepared under strictly aseptic conditions:

|  | % w/w |
|---|---|
| Acetazolamide micronised (sterile)* | 3.50 |
| Chlorbutol BP | 0.50 |
| citric acid monohydrate** | 0.117 |
| sodium citrate dihydrate** | 0.112 |
| sodium citrate 1% solution** qs | |
| hydroxypropylmethylcellulose 2906 USP 4000 cps (sterile) | 3.80 |
| water for injection to | 100.00 |

*average particle size of about 5 microns
**buffers

Citric acid, sodium citrate and chlorbutol were dissolved in 95% of the total water or injection and the solution sterilized. Micronised sterile acetazolamide powder was dispersed in the solution at ambient temperature using a high shear mixer, The hydroxypropylmethylcellulose, previously sterilized, was dispersed in the suspension and then allowed to hydrate over a period of about 15 minutes. The pH was adjusted to between 4.3 and 4.4 with a 1% solution of sterilized sodium citrate. The gel was adjusted to final weight with water for injection and mixed thoroughly.

The resultant gel had a viscosity of 25 poise at a shear rate of 380 second$^{-1}$ and a yield value of 3800–3900 dynes/cm$^2$, both measured by a Ferranti-Shirley viscometer at 25° C.

EXAMPLE 3

The following suspension, gelling in situ at body temperature, was prepared:

|  | % w/w |
|---|---|
| acetazolamide micronised (sterile)* | 3.50 |
| benzalkonium chloride BP | 0.02 |
| citric acid monohydrate | 0.117 |
| sodium citrate dihydrate | 0.112 |
| "Pluronic" F127** | 19.00 |
| sodium citrate/citric acid solution qs | |
| water for injection to | 100.00 |

*average particle size about 5 microns
**"Pluronic" F127 is a polyoxyethylene-polyoxypropylene block copolymer of average molecular weight about 11,500

Citric acid, sodium citrate and benzalkonium chloride were dissolved in 98% of the total water for injection. The "Pluronic" F127 was dispersed in this solution and left to hydrate overnight. The preparation was then thoroughly mixed and the pH adjusted to 4.30 to 4.40 with sodium citrate or citric acid solution as appropriate. The solution was made to 96.5% of the total weight and sterile filtered into a sterile container. The sterile micronised actazolamide was dispersed aseptically in the filtered solution using a high shear mixer.

The resultant suspension had a pH of 4.36 and on heating formed a gel with a sol-gel transition temperature of 30°–32° C. The gel had viscosity of 8 poise at a shear rate of 380 second$^{-1}$ and a yield value of 2310–2320 dynes/cm$^2$, both measured at 34° C. on a Ferranti-Shirley viscometer.

EXAMPLE 4

The following gel was prepared under strictly aseptic conditions:

|  | % w/w |
|---|---|
| acetazolamide micronised (sterile) | 3.50 |
| chlorbutol BP | 0.50 |
| ethylene maleic anhydride resin (EMA) type 91 (sterile) | 0.80 |
| dilute ammonium hydroxide solution (1.75% NH$_3$) | 4.40 |
| water for injection | 90.80 |

The sterile EMA resin was dispersed in 50% of the total water for injection, and the dilute ammonium hydroxide solution stirred in and heated at 95° C. for 15 minutes. The resultant gel was allowed to cool to below 60° C.

The ohlorbutol wad dissolved in the remaining 50% of the water for injection, at a temperature not exceeding 60° C., and sterile filtered into the gel which was mixed slowly.

The sterile micronised acetazolamide powder was thoroughly dispersed in the gel.

The resultant gel had a pH of 4.4.

The viscosity and yield value, both measured by a Ferranti-Shirley viscometer at 25° C., were 11.4 poise (at a shear rate of 380 second$^{-1}$) and 2100 dynes/cm$^2$ respectively.

We claim:

1. A stable, ophthalmic aqueous composition for topical administration, comprising (a) acetazolamide and either (b) a pre-formed, pharmaceutically acceptable, aqueous gel or (c) an aqueous gel-forming liquid capable of forming a pharmaceutically acceptable gel in situ when applied topically to a patient; said composition having a pH of less than 5.0.
2. A composition according to claim 1, having a pH in the range 4.0–4.5.
3. A composition according to claim 2, having a pH in the range of 4.3–4.5.
4. A composition according to claim 1, wherein said acetazolamide used has a particle size of 10 microns or less.
5. A composition according to claim 1, formulated as a pre-formed gel from a pharmaceutically acceptable high molecular weight gel-forming polymer.
6. A composition according to claim 5, wherein said high molecular weight gel-forming polymer is a carboxy vinyl polymer having a molecular weight above 1,000,000, a cellulose ether or an ethylene-maleic anhydride copolymer.
7. A composition according to claim 6, wherein said pre-formed gel has a yield value of 700 to 7000 dynes/cm$^2$.
8. A composition according to claim 1, formulated as a liquid capable of forming a gel in situ when warmed by the body of a patient.
9. A composition according to claim 8, containing as gel-forming agent a polymer of polyoxyethylene-polyoxypropylene block copolymer.
10. A composition according to claim 2, comprising also an antimicrobial agent.
11. A composition according to claim 10, wherein said antimicrobial agent is 1,1,1-trichloro-2-methyl-2-propanol hemihydrate.
12. A composition according to claim 1, comprising from 1 to 10% by weight of said acetazolamide.

* * * * *

UNITED STATES PATENT OFFICE
CERTIFICATE OF CORRECTION

Patent No. 4,888,168　　　　　Dated December 19, 1989

Inventor(s) Angela C. Potts; Mark Gibson

It is certified that error appears in the above-identified patent and that said Letters Patent is hereby corrected as shown below:

Column 2, line 2, "ph" should be --pH--.

Column 2, line 13, "13 weeks" should be --14 weeks--.

Column 2, line 40, "pre-formedppharmaceutical" should be --pre-formed pharmaceutical--.

Column 3, line 58, "righid" should be --rigid--.

Column 4, line 57, "Carbopol in water" should be --carbopol gel in water--.

Column 4, line 58, "As sterile" should be --A sterile--.

Column 5, line 20, "water or injection" should be --water for injection--.

UNITED STATES PATENT AND TRADEMARK OFFICE
CERTIFICATE OF CORRECTION

PATENT NO. : 4,888,168

DATED : December 19, 1989

INVENTOR(S) : Angela C. Potts; Mark Gibson

It is certified that error appears in the above-identified patent and that said Letters Patent is hereby corrected as shown below:

Column 6, line 19, "ohlorbutol wad" should be --chlorbutol was--.

Signed and Sealed this

Twenty-fifth Day of June, 1991

*Attest:*

*Attesting Officer*

HARRY F. MANBECK, JR.

*Commissioner of Patents and Trademarks*